United States Patent [19]

Bartels et al.

[11] 4,333,356

[45] Jun. 8, 1982

[54] MIXING APPARATUS

[75] Inventors: Hermann Bartels, Binningen; Hans-Christian Mez, Basel; Walter Huber, Riehen; Hans-Peter Stolz, Pratteln, all of Switzerland

[73] Assignee: Ciba-Geigy Corporation, Ardsley, N.Y.

[21] Appl. No.: 140,536

[22] Filed: Apr. 15, 1980

[30] Foreign Application Priority Data

Apr. 27, 1979 [CH] Switzerland ............... 3992/79

[51] Int. Cl.³ .................................... G01N 35/08
[52] U.S. Cl. .......................... 73/864.21; 73/864.34; 137/99; 422/63; 422/81
[58] Field of Search ............. 73/423 A; 422/62, 63, 422/64, 65, 67, 81, 82; 364/502, 510; 222/134, 135, 144.5, 145; 137/99, 100; 417/3, 4, 5, 6, 426

[56] References Cited

U.S. PATENT DOCUMENTS

| | | | |
|---|---|---|---|
| 3,398,689 | 8/1968 | Allington | 137/99 |
| 3,570,314 | 3/1971 | Wagner | 73/422 R |
| 3,620,134 | 11/1971 | Conlon et al. | |
| 3,666,420 | 5/1972 | Paatzsch | 422/81 |
| 3,831,618 | 8/1974 | Liston | 422/82 |
| 4,096,972 | 6/1978 | Bartels et al. | 222/135 |
| 4,275,822 | 6/1981 | Juffa | 222/134 |

FOREIGN PATENT DOCUMENTS

| | | |
|---|---|---|
| 3563 | 8/1979 | European Pat. Off. |
| 1950770 | 4/1971 | Fed. Rep. of Germany |
| 2746520 | 4/1978 | Fed. Rep. of Germany |

OTHER PUBLICATIONS

Krottinger et al., "High Speed, Automatic dispenser/diluter, etc.", Journal of Automatic Chemistry, vol. 1, No. 1, pp. 15–21, Oct. 1978.

Mieling et al., "Fully Automated Stopped-Flow Studies with a Hierarchical Computer Controlled System", Analytical Chem., pp. 1686–1693, vol. 48, No. 12, Oct. 1976.

Primary Examiner—S. Clement Swisher
Attorney, Agent, or Firm—Harry Falber

[57] ABSTRACT

A mixing apparatus utilizes piston burettes driven by stepping motors as metering pumps to deliver component liquids to be mixed into a liquid stream in a selectable constant mixing ratio. A computer-based automatic control system is used to control the regulated take up of the respective components by the burettes and the delivery of them to a mixing device. The computer calculates the rates of stepping of the respective motors so that each component is delivered over the same period of time and at a respective uniform rate. The computer also controls associated switching valves via an interface device and may be a desk top machine with keyboard or pre-programmed data input.

11 Claims, 6 Drawing Figures

MIXING APPARATUS

FIELD OF THE INVENTION

The invention relates to a mixing apparatus for producing a stream of liquid comprising two or more components, the stream containing the components in constant mixing ratio. The invention is particularly concerned with mixing apparatus for supplying a flow measurement cell.

BACKGROUND TO THE INVENTION

At present flow measurement cells are supplied virtually exclusively by mixing apparatus operating by the so-called "Stopped Flow" technique. A typical mixing apparatus of this kind is described for example in "Analytical Chemistry", vo. 48, No. 12, Oct. 1976, pp. 1686–1693. One disadvantage of such apparatus is that it comprises metering pumps, e.g. piston-type burettes, driven by a common motor for the liquids which are to be mixed together and consequently, unless the construction of the burettes is modified or the burettes are substituted, the mixing ratio cannot be altered once chosen.

A metering and diluting apparatus providing an adjusting mixing ratio has been proposed primarily for use in biomedical and clinical chemistry. With this apparatus mixtures (dilutions) can be produced having a dilution ratio which is variable within wide limits. This apparatus essentially comprises two piston burettes, controlled by stepping motors, which can be connected to supply vessels or to a mixing vessel by selecting the positions of two three-way valves. An electronic control means controls the burette motors and valves so that the volumes of the two liquids to be mixed which are to be fed into the mixing vessel are automatically taken up by the burettes. The volumes of liquid components are then expelled at a constant speed which can be adjusted manually.

This prior-proposed dilution apparatus is hardly used at all for directly supplying flow measurement cells. In fact, the use of the apparatus for this purpose would pre-suppose that the mixing ratio of the stream of liquid pumped through the measuring cell is constant, and that the volumes of liquid would have to be each expelled by the burettes at a constant speed and synchronously, i.e. at the same time. The burettes would therefore have to start at the same time and stop at the same time. Thus, different metering speeds would obviously be required for different mixing ratios.

These requirements are not satisfied, or can only be partly satisfied, by the prior dilution apparatus. This is particularly due to need for the metering speeds for each new mixing ratio having to be reset afresh by hand. Experience shows that this is very laborious and in any case only rarely proves successful. It is particularly difficult to adjust the speeds with the relatively high degree of precision often needed.

The same disadvantage is true of other known dilution apparatus such as described in U.S. Pat. Nos. 3,800,984 to Phelan and 3,982,667 to Chen, and in German (Federal Republic) Offenlegungschrift No. 19 50 770.

It is an object of the present invention to provide mixing apparatus for producing a stream of liquid comprising two or more components in which the stream contains components in a selected mixing ratio, the stream being homogeneous with respect to its components, and in which automatic control means is provided to control the mixing in accord with input data determining the required mixing ratio.

It is a further object of the invention to provide automatic control means for a mixing apparatus for liquid components that is operable to control the mixing ratio and to control valves and other devices for the take-up of the components for mixing in the required ratio.

SUMMARY OF THE INVENTION

A mixing apparatus for producing a liquid having a plurality of components mixed in a selected ratio comprises flow means for receiving the respective components, and a plurality of metering pumps for the respective components connected to the flow means and operable to cause delivery of the components to the flow means. Each pump has a respective drive motor. The pumps may be piston-type burettes each having its piston coupled to a respective stepping motor as the drive motor so as to sweep a predetermined increment of volume in response to each step of the motor.

In accord with the invention the mixing apparatus comprises as automatic control means connected to the pump motors to control same. The control means has input means for receiving data determining the selected mixing ratio and is responsive to the input data to supply individual signals to the pump motors throughout the same period of time such that the pumps cause delivery to the flow means of quantities of respective components in accord with the selected ratio and each quantity is delivered at a respective uniform rate during this period of time.

The mixing apparatus of the invention is particularly intended for delivering a homogeneous mixed liquid to a flow measurement cell which may constitute or be part of the flow means. The pump may deliver their components to a separate mixing device which, in turn, delivers the mixed liquid to the cell.

In a preferred embodiment the automatic control means includes a computer having an input means, e.g. a keyboard or a pre-loaded store, for entering data. The data may be input in terms of the volumes of the individual components to be mixed, the computer calculating from this data, a period of time during which the required volumes are to be delivered and the respective rates or speeds of operation of the pumps over that period to ensure that each volume is delivered at a uniform rate throughout. Where the pumps are piston burettes driven by stepping motors, the volumes may be expressed in terms of numbers of steps and the delivery rate is controlled by the step rate. The computer calculates the interval for each pump as an integral number of intervals (periods) of a clock pulse source. The computational steps include a routine for obtaining the required numbers of clock pulse intervals to within an allowed percentage error so that the total delivery period is not unduly prolonged.

The computer is coupled to the pumps via an interface device which supplies trains of pulses to the stepping motors to step same, each pulse train having the pulse interval calculated by the computer. The interface device also serves to deliver pulses to set the piston burettes to the required volumes. The automatic control means also control valves and other devices associated with the take up and subsequent delivery of liquid by the piston burettes.

BRIEF DESCRIPTION OF THE DRAWINGS

The invention will now be further described with reference to embodiments of it illustrated in the accompaying drawings in which.

THE PREFERRED EMBODIMENT

Figure 1:
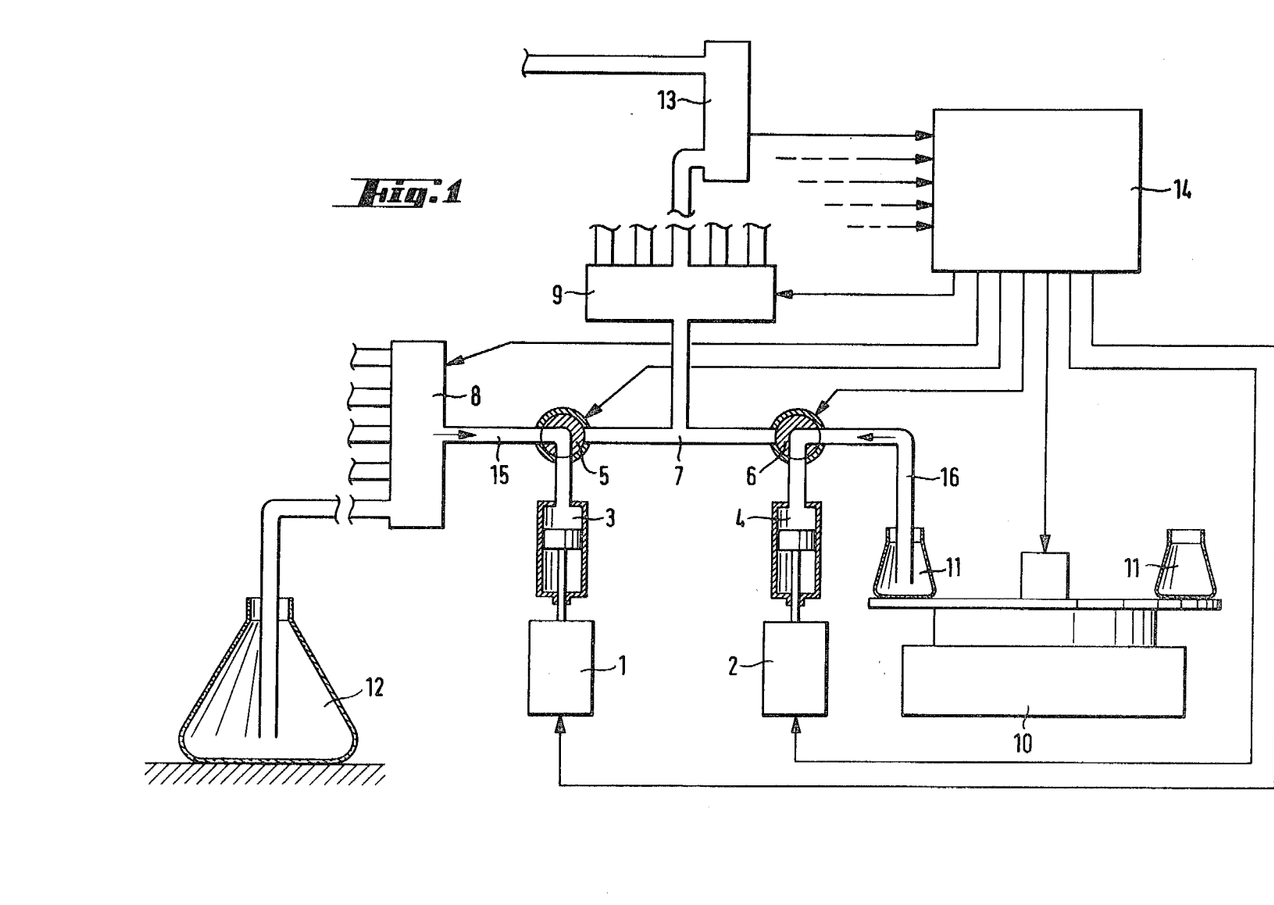
FIG. 1 is a diagrammatic representation of a mixing apparatus of the invention.

The mixing apparatus diagrammatically illustrated in FIG. 1 is intended to mix two liquid components delivered by respective metering pumps constituted by respective piston burettes 3 and 4, the pistons of which are driven by individual stepping motors 1 and 2. The burettes 3 and 4 are connectable to a common mixing device 7 through respective changeover valves 5 and 6, which in a first position connect the burettes to the mixing device and in a second position isolate the burettes from the mixing device 7 and connect them to respective sources of liquid components to be mixed. The valves are controlled together by a common motor 17, shown in FIG. 2. The burette 3 is connected through valve 5 and a feed line 15 to the common outlet port of a controllable multi-way valve 8 by means of which one of a number of liquid component sources is connectable to the burette 3. One such source 12 is shown. The other burette 4 is connectable via valve 6 and a feed line 16 to a sample changer device 10 providing a plurality of component sources for burette 4. The sample changer is of the rotary plate type carrying a number of sources 11, two of which are shown and is controllable to bring a selected source to an operating station where liquid can be taken up by the burettte 4.

The mixing device 7, which is shown as a simple T-member, has its arms connected to respective valves 5 and 6 and its leg portion to the common inlet of a controllable multi-way valve 9 which is selectively operable to deliver a stream of mixed liquid to a selected one of a plurality of flow measurement cells 13, one of which is shown.

The whole apparatus thus far described is controlled by an automatic control system 14 further described below. As indicated by the arrowed lines system 14 provides control signals to the motors 1 and 2 of the burettes, the change-over valves 5 and 6 (more specifically to their common drive motor 17) and to the multi-way valves valves 8 and 9. The system 14 may also receive control signals from the flow measurement cells 13.

The piston burettes and change-over valves and the various drive motors may be identical or similar to those in the mixing apparatus known as the "Hamilton-Dilutor" made by the firm Hamilton Bonaduz AG, Bonaduz, Switzerland.

The general method of operation of the apparatus will be described initially without going into detail of the control system 14 that actuates the various valves and motors to perform the method.

By means of the multi-way valve 8 and by suitable positioning of the sample changer 10, the supply containers 11 and 12 with the desired liquids to be mixed together are selected and connected by the feed lines 15 and 16 to the change-over valves 5 and 6. The valves 5 and 6 are then brought into the second position shown in FIG. 1, in which they connect the feed lines to the piston burettes 3 and 4 respectively. The latter are then actuated and each sucks in the required volume of sample. Subsequently, the valves 5 and 6 are switched over and the burettes then simultaneously expel the two liquid samples into the mixing device 7. From there, the mixture passes through the multi-way valve 9 and, depending on the position of the latter, into the flow measurement cell 13 desired and from there into any discharge line.

To ensure that the mixture of liquids passing into the flow measurement cell 13 is as homogeneous as possible, it is essential that the two burettes expel their respective volumes of sample at uniform speed and particularly in synchronism, i.e. within the same period of time. The speeds and metering outputs of the two burettes naturally depend on the two volumes of sample used or on their proportions. The control system 14 therefore contains means which enable the desired volumes of sample to be preselected and, in a manner to be described hereinafter, using these preselected values, calculate the simultaneous discharge period and the piston speeds of the two burettes, and control the burettes accordingly.

The apparatus shown in FIG. 1 is of wide applicaton. With the multi-way valves 8 and 9 and the sample changer 10, the desired sample (source) liquids can be selected automatically, e.g. under control of a program in the control system 14, or a plurality of different flow measurement cells can be supplied automatically. It will be appreciated that, for less demanding purposes, the multi-way valves and/or the sample changer may be omitted.

Figure 2:
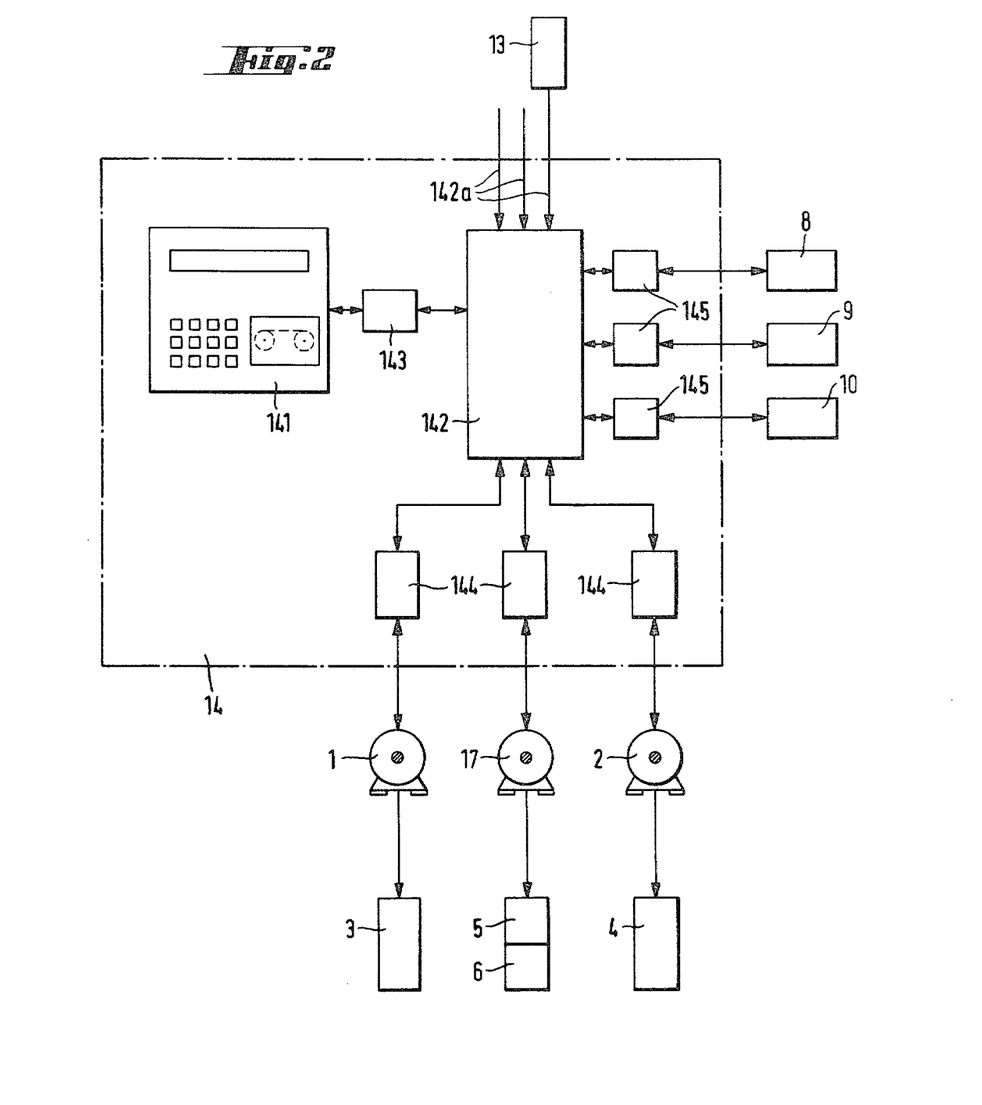
FIG. 2 is a block diagram of the automatic control means employed in the apparatus of FIG. 1.

The automatic control system 14 is shown in more detail in FIG. 2. It comprises a programmable computer 141, a main interface device 142 in two-way communication with the computer 141 through a subsidiary connecting interface device 143, and a series of drive circuits 144 and 145 in two-way communication with the main interface device 142. The interface 143 constituting the connection between the computer 141 and the main interface device 142 could be incorporated in the main interface. The drive circuits 144 connect the main interface device 142 to the drive (servo) motors 1 and 2 for the two piston burettes 3 and 4 and the two change-over valves 5 and 6 controlled by common motor 17. Likewise the two multi-way valves 8 and 9 and the sample changer 10 are controlled from the main interface device through individual drive circuits 145. Main interface device 142 is also provided with inputs 142a to which the various flow measurement cells 13, mentioned in connection with FIG. 1, can be connected to supply signals to the interface. Obviously, there are also various response connections and the like in the system, but these are not essential to the understanding of the method of operation of the apparatus and are therefore not shown.

The programmable computer 141 may, for example, be a programmable desk computer such as the HP-9815A computer made by Hewlett Packard, Palo Alto, Calif., USA.

The main interface device 142 may, for example, be constructed around a microcomputer, such as a DCE-1 microcomputer made by Data Applications International S.A., Brussels, Belgium, as the central processing unit with a plurality of clocks and three parallel I/O (input/output) interfaces and a serial I/O interface, an analog multiplexer feeding an analog-to-digital converter and a digital multiplexer for reading in digital form.

The interface device 143 is a conventional serial I/O interface. The various drive circuits 144 and 145 may be designed using conventional techniques and obviously their specific construction depends on the nature of the motors or valves which are to be controlled, and is within the compass of those skilled in the art.

The described control system 14 is organised with distributed processing in which the computer 141 is the command or instruction giver, whilst the main interface device 142 ensures that the instructions received from the computer are carried out and reports this back to the computer. A similar control or method of organization is described, for example, on pages 1686–1693 of "Analytical Chemistry", Vol. 48, No. 12, October 1976.

Considering now the operation of the automatic control system 14 in greater detail, it has two main conditions of operation. In one the burettes take up required volumes of liquid and in the other the pistons are actuated by respective trains of pulses to their stepping motors to expel desired volumes over the same period of time, and each volume being expelled at a uniform rate over that period by selecting the pulse interval of the respective pulse train so that a homogeneous stream of liquid having the selected mixing ratio is obtained. Since each burette piston sweeps a known increment of volume for each step of its drive motor the required volumes can be represented in terms of numbers of step increments.

In the simplest case, the desired volumes of the two sample components which are to be mixed together are fed into the computer using the keyboard. The computer then calculates the time intervals between the individual step pulses of the respective pulse trains for the two stepping motors of the burettes and passes the data relating to the volumes and intervals, together with an "execute" command, to the main interface device. The latter then autonomously carries out a burette cycle, by causing the burettes to suck in the desired volumes at the maximum speed—starting from a defined initial position obtained by a resetting routine—and then expel them again at the speeds determined by the above mentioned pulse intervals. The step pulses for the burette motors 1 and 2 and the control impulses for the valve servo motor 17 are produced by the main interface device 142 timed to the internal clocks thereof and in accord with the data obtained from the computer. At the end of the burette cycle, this is again reported back to the computer.

The above operations are hereinafter summarised more clearly with reference to the flow diagrams of FIGS. 3 and 4.

The input data to the computer 141 may be entered via its keyboard or via already stored data. This data may be in terms of volumes to be mixed thereby determining the mixing ratio required or can be in terms of proportions for a given total volume, i.e. directly giving the mixing ratio. In whatever manner the data is presented, the computer makes the calculations mentioned above. Further consideration is given below to optimising such calculations to provide delivery in a reasonable period of time where each pulse interval is to be made equal to an integral number of clock pulse intervals.

Figure 4:
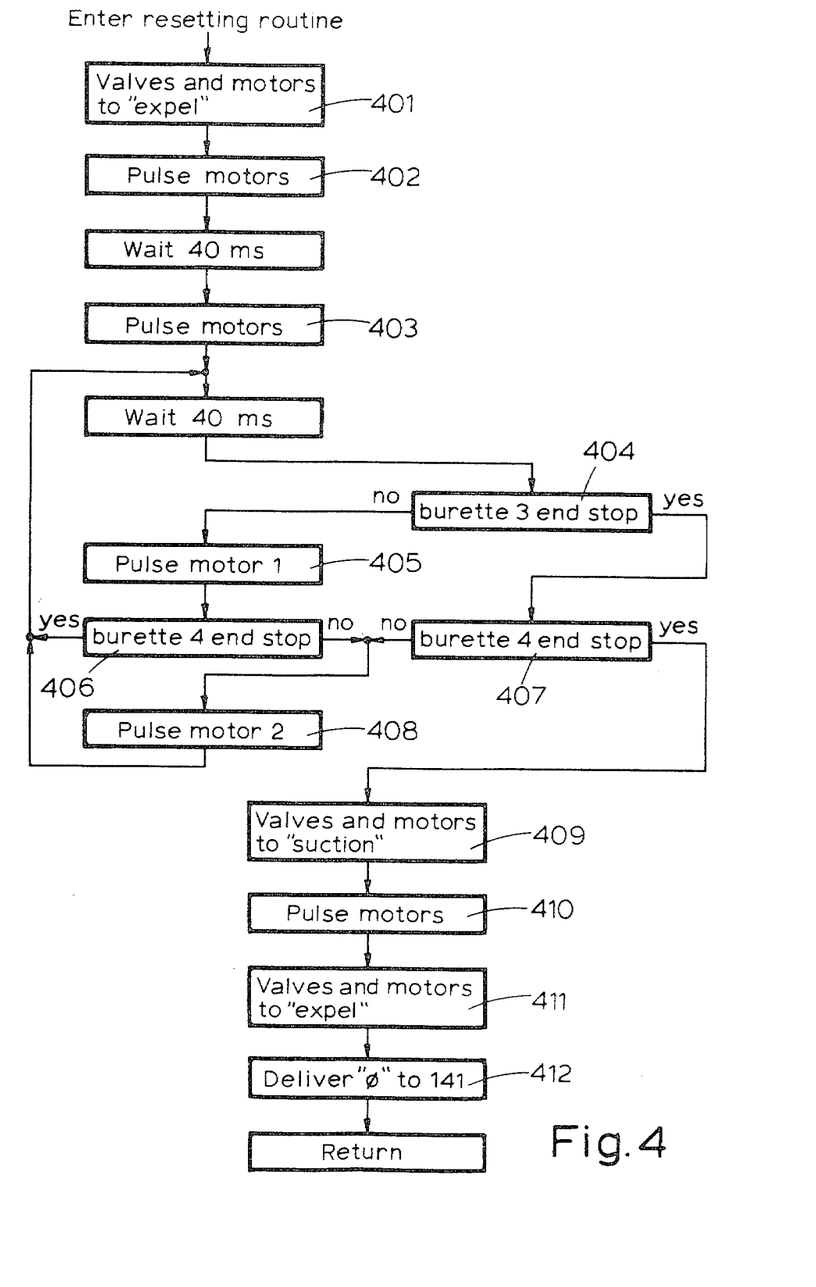
FIG. 4 is a flow diagram illustrating a resetting routine for the apparatus of FIGS. 1 and 2.

FIG. 4 shows more fully the resetting routine which is entered and completed before the burettes actually take up liquid from the sources 11 and 12 of FIG. 1 as selected by signals from the control system to the multiway valve 8 and sample changer device 10. In FIG. 4 certain of the routine steps are legended in abbreviated form and these steps are listed more fully below.

401: Bring the valves 5 and 6 into the "expel" position connecting the burettes to the mixing device 7. Monitor the valve positions. Set the stepping direction of the stepping motors 1 and 2 to the expel or delivery direction.

402 & 403: Deliver one pulse to each of motors 1 and 2.

404: Is the burette 3 at its upper end stop position as seen in FIG. 1?

405: Deliver one pulse to motor 1.

406 & 407: Is the burette 4 at its upper end stop position as seen in FIG. 1?

408: Deliver one pulse to motor 2.

409: Bring the valves 5 and 6 to the "suction" position connecting the burettes to the liquid component sources. Monitor the valve position. Set the stepping direction of the motors 1 and 2 to the "suction" or take up direction.

410: Deliver sixteen (16) pulses to each of motors 1 and 2.

411: Repeat step 401.

412: Deliver a "$\phi$" to the computer 141 indicating end of resetting routine.

The foregoing routine has established an initial position for the burette piston of each metering pump. From this initial position the burettes can undertake the burette cycle to take in the volumes of the component liquids required and to expel them at the calculated rates. The volumes to be mixed can be represented in terms of the equivalent number of motor steps required to sweep the volumes as will now be described.

Pulse numbers $I_1$ and $I_2$ hereinafter denote the measured, adjusted or pre-programmed samples volumes in multiples of the smallest unit of volume which can be taken up or released by a burette 3 or 4 and which is determined by the advance of the burette piston by one step. In a practical embodiment by way of example, the stroke of the burettes is limited to a maximum of 800 steps. Therefore, the sample volume $I_1$ or $I_2$ can be up to a maximum of 800. Theoretically, the mixing ratios of from 1:800 to 800:1 can be obtained thereby. However, in practice, the ratio of the volume of the measurement cell to the total sample volume also plays a part, with the result that practical mixing ratios of from 1:80 to 80:1 are obtained.

The timing numbers $T_1$ and $T_2$ denote the intervals between two stepping pulses of the pulse train supplied to expel a sample volume for the burette stepping motors 1 and 2 respectively. $T_1$ and $T_2$ are measured in terms of the number of clock pulse intervals of a real time clock in the main interface device 142. There is an inversely proportionate relationship between the pulse numbers $I_1$ and $I_2$ and the timing numbers $T_1$ and $T_2$. In a manner to be described hereinafter, the timing numbers are determined, by the desk computer 141, from the pulse numbers and are passed on to the main interface device. The basic timing period of the real time clock in the microcomputer used here is 64 $\mu$sec, corresponding to a frequency of 15.625 kHz. Because the two volumes represented by $I_1$ and $I_2$ have to be expelled simultaneously so as to start and end together it is seen that it is necessary to satisfy the relationship:

$I_1 \cdot T_1 = I_2 \cdot T_2 =$ total period.

Because all the factors are to be integral numbers and the mixing ratio $I_1/I_2$ can vary between the limits mentioned above, it is desirable to select $T_1$ and $T_2$ also to be integral in the inverse ratio without making the total period excessive. A way of doing this within selected limits is further discussed below.

Figure 5:
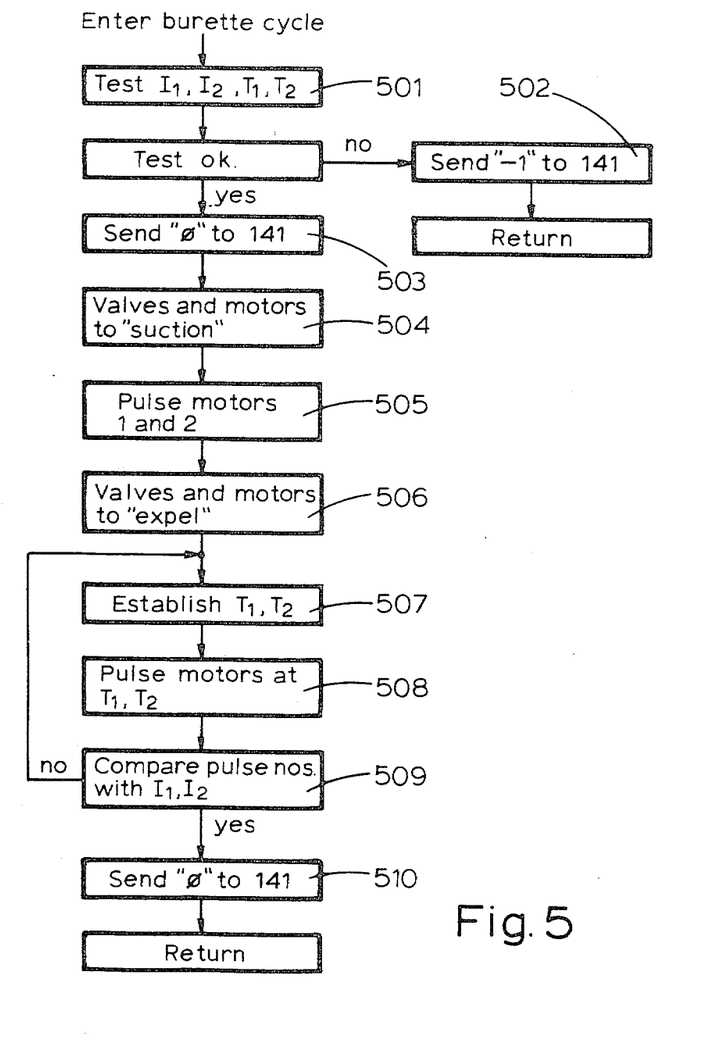
FIG. 5 is a flow diagram illustrating an operational burette cycle in the mixing apparatus.

Once the values of $I_1$, $I_2$, $T_1$ and $T_2$ are all available the burette cycle can commence. In the example given both $I_1$ and $I_2$ should lie below the maximum value of 800. The timing numbers may be zero ($\phi$) or otherwise not less than 50 ($\geq 50$) for reasons that will become clearer hereinafter. The flow diagram of the burette cycle is shown in FIG. 5. The legends for certain steps are in abbreviated form and are set out more fully below:

- 501: Test pulse numbers $I_1$, $I_2$ for reliability ($\leq 800$) Test timing numbers $T_1$, $T_2$ for reliability ($\phi$ or $\geq 50$).
- 502: Send "−1" to desk computer as an error signal.
- 503: Send "$\phi$" to desk computer indicating "proceed".
- 504: Bring the valves 5 and 6 into the "suction" position connecting the burettes to the selected component sources. Monitor the valve position. Set the stepping direction of the motors 1 and 2 to the "suction" or take up direction.
- 505: Deliver $I_1$ stepping pulses to motor 1. Deliver $I_2$ stepping pulses to motor 2. The same pulse interval is used for both motors and in the example given is made equal to fifty (50) clock pulse intervals.
- 506: Bring the valves 5 and 6 into "expel" position connecting the burettes to the mixing device 7. Set the stepping direction of the stepping motors to the "expel" or delivery direction.
- 507: Initialise first hardware timer (counter)—not shown—with timing number $T_1$. Initialise second hardware timer (counter)—not shown—with timing number $T_2$.
- 508: At end of $T_1$ clock pulse intervals supply pulse to motor 1. At end of $T_2$ clock pulse intervals supply pulse to motor 2.
- 509: Compare the number of pulses so far delivered to motor 1 with $I_1$; number $= I_1$? Compare the number of pulses so far delivered to motor 2 with $I_2$; number $= I_2$?
- 510: Send "$\phi$" to desk computer indicating delivery of the component volumes to the mixing device 7 is complete.

Referring to steps 507, 508 and 509, these steps proceed separately for the two burettes. It will be seen that the loop in which these steps are included result in a train of pulses, $I_1$ in number, being delivered to motor 1 at a step pulse interval of $T_1$ clock pulse intervals and a train of pulses, $I_2$ in number, being delivered to motor 2 at a step pulse interval of $T_2$ clock pulse intervals, thereby delivering the components in the same period of time.

As already stated, the timing numbers $T_1$ and $T_2$ which determine the intervals between the stepping pulses for the two burettes are calculated by the desk computer from the two pulse numbers $I_1$ and $I_2$. A 100% accurate mixing ratio would be obtained if the timing numbers for the two burettes were precisely inversely proportional to the pulse numbers. However, if the pulse numbers are aliquant (e.g. 800:761), this procedure would lead to undesirably long metering times (i.e. the total delivery period) as only integral timing numbers can occur.

For the piston burettes and associated stepping motors used in the exemplified embodiment, a minimum time interval between the individual stepping pulses of 3.2 msec., corresponding to 50 basic clock periods, is required. This minimum interval forms the upper limit for the metering speed.

According to a preferred feature of the invention, the finding of the timing numbers is improved in that by allowing a small (e.g. 0.1%) error substantially shorter metering times can be obtained. For this purpose, starting from the minimum value of 50, the timing number for the larger sample volume or the larger pulse number $I_1$, e.g. $T_1$, is increased by one repeatedly until the timing number $T_2$ for the smaller volume or pulse number $I_2$, obtained by the formula $T_2 = I_1 \cdot T_1 / I_2$, differs from an integer by not more than a certain extent which, in this case, is taken to be the difference between $T_2$, which will normally not be an integer, and the integer, the difference being expressed as a percentage of the calculated value, e.g. not more than 0.1%. With this method, for example, the timing numbers 58 and 61 are found for the pulse numbers 800 and 761 with an error of 0.05%, leading to a total metering time of 3 sec. as compared with 39 sec. when the absolutely precise calculation is used.

Figure 6:
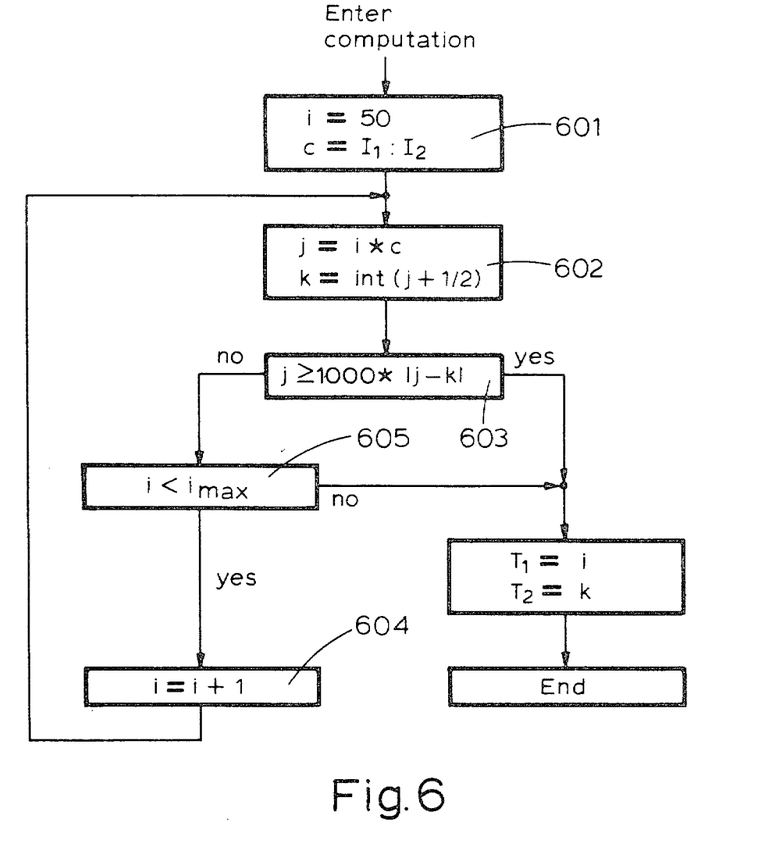
FIG. 6 is a flow diagram illustrating a calculation routine performed by the automatic control system.

The timing numbers $T_1$ and $T_2$ are calculated in the desk computer 141 which can, for this purpose, be programmed to perform a set of calculational steps according to the flow diagram illustrated in FIG. 6.

In FIG. 6 it is seen in step 601 that a minimum value $i = 50$ is assigned to the pulse interval for large pulse number $I_1$, and the ratio $C = I_1/I_2$ calculated. A value $j$ representing the pulse interval. (i.e. $T_2$) is then calculated in steps 602 ($j = i.c$) and the usually non-integral number thus obtained is subject to a routine for calculating the integral component $k$ of the number ($j + \frac{1}{2}$). The operator "int" in step 602 represents a routine for this purpose. Step 603 is a calculation of the difference $|j - k|$ expressed as being not greater than a desired percentage of $j$. In step 603 the error allowed is 0.1%. If step 603 is satisfied the numbers $i$ and $k$ are used for $T_1$ and $T_2$. If the step is not satisfied, and, providing the value $i$ has not reached a value $i_{max}$, $i$ is incremented by one at step 604 and the set of computational steps repeated, $i$ being increased by one each time until either the allowed percentage error is satisfied at step 604 or at step 605 the maximum value $i_{max}$ has been reached in which case $i_{max}$ and the just calculated value of $k$ are used for $T_1$ and $T_2$ respectively.

$i_{max}$ is a randomly selected threshold value for limiting the metering time.

The volumes to be metered may be fed into the computer 14 afresh each time for each mixing operation but, as already mentioned, instead of the volumes being fed in manually from the keyboard, they could also be pre-programmed by means of the program store of the desk computer and then be fed in automatically. This would then make it very easy to carry out series of mixing or diluting operations—e.g. with varying ratios by volume—fully automatically. If the apparatus is provided with sample changers and/or multi-way valves, different liquids can also be mixed automatically and, if required, the mixtures can also be directed to different flow measuring cells. Using the analog inputs of the main interface device 142 it is also possible to control the individual mixing operations as a function of the measured data delivered by the measuring cells. The desk computer merely has to be programmed accordingly in order to do this.

Figure 3:
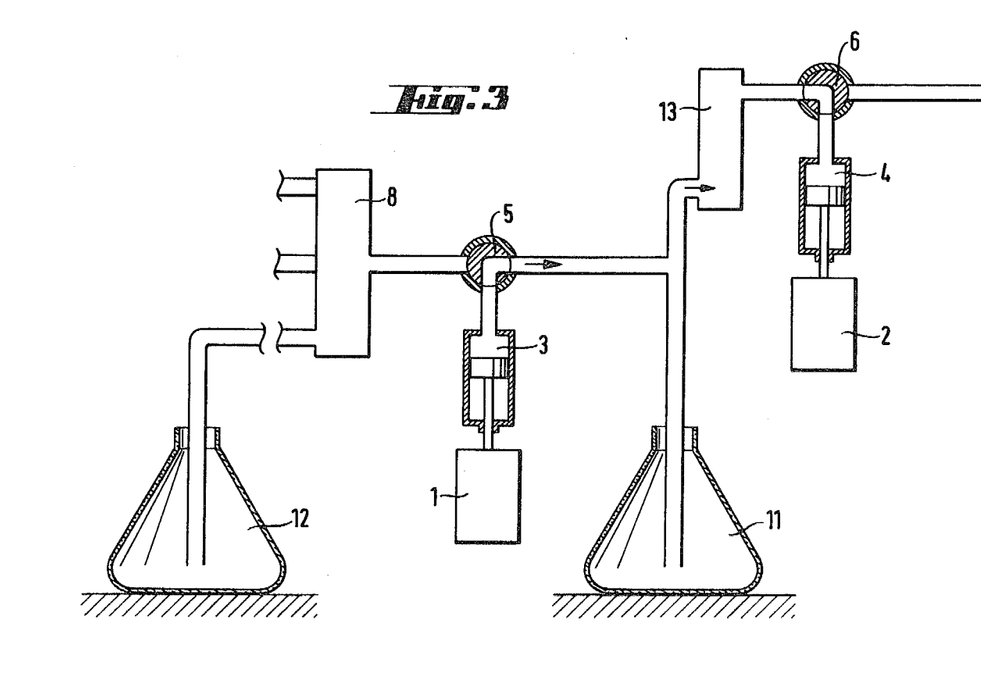
FIG. 3 is a partial diagrammatic representation of a modified mixing apparatus.

FIG. 3 shows a variant of the apparatus according to the invention. It is like the apparatus of FIG. 1 in that it also comprises two burettes 3 and 4 with their stepping motors 1 and 2, two change-over valves 5 and 6, a multiway valve 8, a measurement cell 13 and two sample supply vessels 11 and 12. The motors and valves are controlled by automatic control means (not shown in FIG. 3) of the kind that has been described.

The difference from the embodiment according to FIG. 1, apart from the simplified construction, is in the connection of the burettes, supply vessels and measurement cell to one another. As in FIG. 1 the burette 3 is selectively connectable to the sample vessel 12 or the flow measurement cell 13 by means of valve 5. The burette 4, however, is connected to its sample vessel 11 via the measurement cell 13 in one position of the valve 6, the other valve position connecting the burette 4 to a discharge pipe. Thus, in order to mix the two sample liquids, the burette 3, after taking up the required volume of one of the liquids, has to expel it as before, whilst the burette 4 has to take up liquid during the period burette 3 is expelling it at a rate that is greater than that of expulsion by burette 3 by an amount corresponding to the desired volume of the other liquid to be drawn from the vessel 11.

This alternative embodiment of the apparatus is particularly advantageous if there are only small quantities of one of the sample liquids (in vessel 11) available or if only small quantities thereof are to be mixed in. The burette motors are controlled in the same way as in the embodiment according to FIGS. 1 and 2.

In the embodiment illustrated in FIG. 1 the mixing device 7 consists of a simple T-member. It will be appreciated that a mixing spiral, an X-Y mixer or a flow vortex mixer, for example, could be used instead. Mixers of these kinds are described, for example, in Helv. Chim. Acta XL, p. 907, 1957, and The Journal of Automatic Chemistry, Vol. 1, No. 1, October 1978, pp. 15–21.

Moreover, it is, of course, also possible to use three of more burettes instead of the two shown. The control of these burettes would be in accord with the principles explained in connection with the use of two burettes.

What is claimed is:

1. In a mixing apparatus for producing a liquid having a plurality of components mixed in a selected ratio which comprises flow means for receiving the respective components, and a plurality of metering pumps for the respective components connected to said flow means and operable to cause delivery thereto of the components, each pump having a respective stepping motor as a drive motor and comprising a piston burette, the piston of which is driven by said stepping motor to sweep a predetermined increment of volume in response to each step of the stepping motor, the improvement comprising an automatic control means connected to the pump motors to control same and being operable to supply individual control signals thereto as respective trains of pulses, said control means having input means for receiving input data determining the selected mixing ratio and including computer means (a) being responsive to such input data to compute and establish the pulse interval for each pulse train such that the pumps cause quantities of the respective components to be delivered to said flow means in the same period of time in accord with said selected ratio and at a respective uniform rate during said period and (b) being arranged to compute initial piston positions for the burettes in accord with the quantities of the respective components to be delivered to the flow means in accord with said selected ratio; and said automatic control means further including an interface device connected to each stepping motor and responsive to commands generated by the computer means to supply pulses to the associated stepping motor to establish the initial position of the associated burette piston and to subsequently control the supply of the train of pulses to the stepping motor to cause delivery of the associated component to said flow means.

2. Apparatus as claimed in claim 1 in which the automatic control means includes a pulse clock source and the computer computes the pulse interval for each pulse train as an integral multiple of the clock pulse interval.

3. Apparatus as claimed in claim 2 in which the computer means is arranged to perform a set of computational steps comprising: computing from input data determining the ratio of the quantities of two components to be delivered to the flow means by first and second metering pumps and from a first number of clock source intervals assigned as the pulse interval for the pulse train to the stepping motor of said first pump, a second number (not necessarily integral) of clock pulse intervals required to be assigned to the pulse interval of the pulse train to the stepping motor of said second metering pump to cause delivery to said flow means in the same period of time of the quantities of respective components by said first and second pumps in said selected ratio, and computing the extent by which the second number deviates from an integer; the computer means being arranged to repeat this set of computational steps incrementing the first number employed in the previous set of steps by one until the extent of deviation of the second number from an integer does not exceed a predetermined limit, and to establish the integer so obtained as the number of clock pulse intervals constituting the pulse interval for the train of pulses to the stepping motor of said second pump.

4. Apparatus as claimed in claim 3 in which, in response to the input data, said computer means is arranged to express the ratio of the components pertaining to said first and second pumps in terms of respective numbers of step increments of the piston burettes and use the ratio of said numbers of step increments in performing said set of computational steps.

5. Apparatus as claimed in claim 1 in which said interface device includes a microprocessor device providing two-way communication between said computer means and each metering pump, whereby the automatic control system operates with distributed processing.

6. Apparatus as claimed in claim 1 in which said flow means comprises a mixing device connected to each piston burette through a respective controllable change-over valve, said automatic control means being arranged to control said change-over valve and being operable in a first condition to set said change-over valves to first positions connecting the piston burettes to the mixing device for the delivery thereto of quantities of respective components in accord with the selected ration, and being operable in a second condition to set said change-over valves to second positions in which the piston burettes are able to receive further quantities of the respective components.

7. Apparatus as claimed in claim 6 further comprising a controllable multi-way valve connected to one of said change-over valves so as to be in communication with the associated piston burette associated with said one change-over valve in the second position of the latter, said automatic control means being arranged to control said multi-way valve to select one of a plurality of liquid component sources for connection to said associated piston burette during said second condition of said automatic control means.

8. Apparatus as claimed in claim 1 in which each piston burette is connected to said flow means through a respective change-over having a first position in which the associated piston burette is in communication with said flow means for causing delivery thereto of a respective component and having a second position in which the associated piston burette is isolated from the flow means for setting to an initial piston position prior to such delivery, said automatic control means being arranged to control the change-over valves and being operable in first and second conditions to set all the valves to said first positions respectively.

9. Apparatus as claimed in claim 8 further comprising a controllable multi-way valve connected to one of said change-over valves to be coupled to the associated piston burette in the second position of said one change-over valve, automatic control means being arranged to control said multi-way valve to select one of a plurality of component sources.

10. Apparatus as claimed in claims 6 or 8 in which one of said change-over valves is connected to a discharge line in said second position thereof and further comprising an inlet line for a component connected to said one change-over valve through said flow means.

11. Apparatus as claimed in claim 1 further comprising a sample changer device for locating a selected one of a plurality of vessels at an operating station and an inlet line for one of said metering pumps located at said station to take up liquid from a vessel selectively located at said station, the sample changer being connected to said automatic control means for selective location of said vessels at said operating station.

* * * * *